(12) United States Patent
Tabata et al.

(10) Patent No.: US 11,097,072 B2
(45) Date of Patent: Aug. 24, 2021

(54) NEBULIZER MESH SELECTION METHOD, APPARATUS, AND PROGRAM

(71) Applicant: OMRON HEALTHCARE CO., LTD., Muko (JP)

(72) Inventors: Makoto Tabata, Kyoto (JP); Takao Terada, Kyoto (JP); Kei Asai, Kyoto (JP); Masao Maeda, Kyoto (JP); Yusuke Kato, Kyoto (JP)

(73) Assignee: OMRON HEALTHCARE CO., LTD., Kyoto (JP)

( * ) Notice: Subject to any disclaimer, the term of this patent is extended or adjusted under 35 U.S.C. 154(b) by 323 days.

(21) Appl. No.: 15/048,350

(22) Filed: Feb. 19, 2016

(65) Prior Publication Data
US 2016/0166779 A1 Jun. 16, 2016

Related U.S. Application Data

(63) Continuation of application No. PCT/JP2014/074928, filed on Sep. 19, 2014.

(30) Foreign Application Priority Data

Sep. 24, 2013 (JP) .............................. JP2013-196572

(51) Int. Cl.
*A61M 11/00* (2006.01)
*G16H 20/10* (2018.01)
(Continued)

(52) U.S. Cl.
CPC ......... *A61M 11/003* (2014.02); *A61M 11/005* (2013.01); *G16H 10/60* (2018.01);
(Continued)

(58) Field of Classification Search
USPC ....................................................... 705/2, 3
See application file for complete search history.

(56) References Cited

U.S. PATENT DOCUMENTS

| | | | |
|---|---|---|---|
| 2010/0089394 A1* | 4/2010 | Sakurada | A61B 5/4839 128/203.14 |
| 2010/0281020 A1* | 11/2010 | Drubner | G06Q 30/08 707/722 |

(Continued)

FOREIGN PATENT DOCUMENTS

| CN | 101678184 A * | 3/2010 | ............. A61B 5/087 |
|---|---|---|---|
| CN | 101678184 A | 3/2010 | |

(Continued)

OTHER PUBLICATIONS

Martin Knoch & Manfred Keller (2005) The customised electronic nebuliser: a new category of liquid aerosol drug delivery systems, Expert Opinion on Drug Delivery, 2:2, 377-390, DOI: 10.1517/17425247.2.2.377 (Year: 2005).*

(Continued)

*Primary Examiner* — Joshua B Blanchette
(74) *Attorney, Agent, or Firm* — Oliff PLC

(57) ABSTRACT

With a nebulizer mesh selection method it is possible to achieve optimal treatment which fits a medicine and a patient. A nebulizer mesh selection method includes a step of acquiring a medicine attribute, by a computer, a step of acquiring a patient breathing ability, a step of selecting a mesh that corresponds to the acquired medicine attribute and patient breathing ability based on a mesh selection table in which a predetermined mesh corresponds to a combination of a medicine attribute and a patient breathing ability, and a step of outputting the selected mesh.

10 Claims, 5 Drawing Sheets

(51) Int. Cl.
*G16H 10/60* (2018.01)
*B05B 17/00* (2006.01)

(52) U.S. Cl.
CPC ......... *G16H 20/10* (2018.01); *A61M 2207/10* (2013.01); *A61M 2209/02* (2013.01); *B05B 17/0646* (2013.01)

(56) References Cited

U.S. PATENT DOCUMENTS

| | | | | |
|---|---|---|---|---|
| 2012/0266870 | A1* | 10/2012 | Denyer | A61M 15/0085 128/200.14 |
| 2014/0000599 | A1* | 1/2014 | Dyche | A61M 16/14 128/203.14 |

FOREIGN PATENT DOCUMENTS

| | | | |
|---|---|---|---|
| JP | H07-256170 | A | 10/1995 |
| JP | 2002-165883 | A | 6/2002 |
| JP | 2004-249208 | A | 9/2004 |
| JP | 2004249208 | A * | 9/2004 |
| JP | 2006-297226 | A | 11/2006 |
| JP | 2008-229356 | A | 10/2008 |
| JP | 2008-301847 | A | 12/2008 |
| JP | 2012-000145 | A | 1/2012 |
| WO | 2012123919 | A2 | 9/2012 |

OTHER PUBLICATIONS

Hsiun-Ing Chen and Chen-Su Kuo (1989) Relationship between respiratory muscle function and age, sex, and other factors, J Appl Physiol (1985). Feb. 1989;66(2):943-8. (Year: 1989).*
A Discriminant Analysis Applied to Methacholine Bronchoprovocation Testing Improves Classification of Patients as Normal, Asthma, or COPD Greenspon, Lee W. et al. CHEST , vol. 102 , Issue 5 , 1419-1425. (Year: 1992).*
Renee Dilulio, RT Magazine, "The Right Fit: Choosing the Best Nebulizer for Your Patient," Dec. 21, 2007 (Year: 2007).*
Dec. 22, 2014 Search Report issued in International Patent Application No. PCT/JP2014/074928.
Apr. 25, 2018 Office Action issued in Chinese Patent Application No. 2014800511698.
Sep. 23, 2020 Office Action issued in Indian Patent Application No. 201617011669.

* cited by examiner

| | MEDICINE ATTRIBUTES | | | | | | | | |
|---|---|---|---|---|---|---|---|---|---|
| | 1 | 2 | 3 | 4 | 5 | 6 | 7 | 8 | 9 |
| PATIENT BREATHING CAPACITY 1 | •••• | •••• | •••• | •••• | •••• | •••• | •••• | •••• | •••• |
| 2 | •••• | •••• | •••• | •••• | •••• | •••• | •••• | •••• | •••• |
| 3 | •••• | •••• | •••• | •••• | •••• | •••• | •••• | •••• | •••• |
| 4 | •••• | •••• | •••• | •••• | •••• | •••• | | | |
| 5 | •••• | •••• | •••• | •••• | •••• | | | | |
| 6 | •••• | •••• | •••• | •••• | | | | | |
| 7 | •••• | •••• | •••• | | | | | | |
| 8 | •••• | •••• | | | | | | | |
FIG. 5
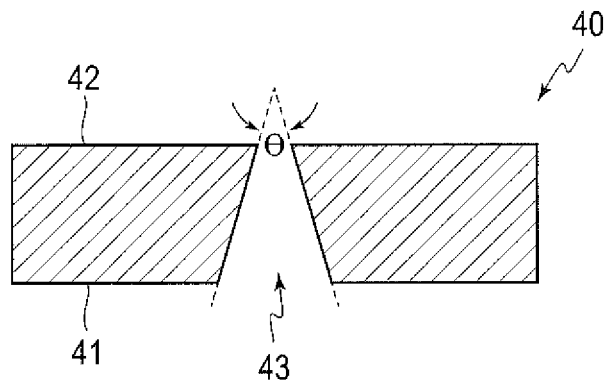
FIG. 6A
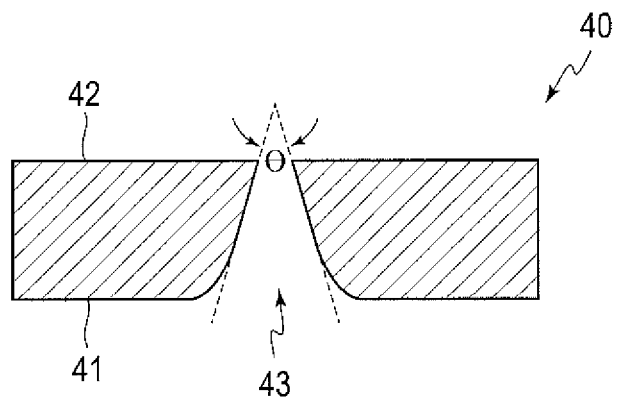
FIG. 6B

NEBULIZER MESH SELECTION METHOD, APPARATUS, AND PROGRAM

TECHNICAL FIELD

The present invention relates to nebulizer mesh selection methods, apparatuses, and programs.

BACKGROUND ART

Liquid spray apparatuses (nebulizers) that atomize and eject liquid such as medicine are roughly divided into compressor nebulizers provided with a compressor and ultrasonic nebulizers provided with an ultrasonic oscillator. Representative ultrasonic nebulizers include mesh nebulizers that atomize medicine by instantly pushing out the medicine from fine mesh holes.

In general, a mesh nebulizer is provided with a liquid storage portion that stores liquid, a mesh having a large number of fine holes, and an oscillation source disposed so as to come into contact with the mesh. The liquid is supplied from the liquid storage portion to a space between the mesh and the oscillation source. The liquid supplied to the space between the mesh and the oscillation source is sprayed to the outside through the fine holes as a result of oscillation of the oscillation source. Conventional liquid spray apparatuses are disclosed in JP 2006-297226A (Patent Literature 1) and JP 7-256170A (Patent Literature 2), for example.

In the mesh nebulizers, the mesh is an important member that significantly affects the particle diameter and the amount of spray of the liquid medicine to be sprayed. For example, it is known that in order to reduce the spray particle diameter, the hole diameter of the mesh is reduced, and in order to increase the amount of spray, the number of holes of the mesh is increased or the hole shape of the mesh is formed such that the medicine can be easily ejected.

CITATION LIST

Patent Literature

Patent Literature 1: JP 2006-297226A
Patent Literature 2: JP 7-256170A

SUMMARY OF INVENTION

Technical Problem

However, in the conventional nebulizer treatment, the mesh is not replaced so as to fit a medicine and a patient. One of the reasons for this is that it is not easy for patients, pharmacists, or the like to determine what kind of mesh to use so as to fit medicines and patients. In addition, although the amount of spray or the like can be changed by adjusting the main body of the nebulizer, this adjustment is left to patients, and better treatment has been desired.

Therefore, a problem for the present invention lies in provision of a nebulizer mesh selection method with which it is possible to achieve optimal nebulizer treatment that fits a medicine and a patient. Specifically, a method is provided for selecting an optimal nebulizer mesh that fits a medicine and a patient from among nebulizer meshes having different hole diameters, numbers of holes, and hole shapes.

Solution to Problem

A nebulizer mesh selection method according to the present invention includes:

a step of acquiring a medicine attribute, by a computer;
a step of acquiring a patient breathing ability;
a step of selecting a mesh that corresponds to the acquired medicine attribute and patient breathing ability based on a mesh selection table in which a predetermined mesh corresponds to a combination of a medicine attribute and a patient breathing ability; and
a step of outputting the selected mesh.

In order to perform optimal nebulizer treatment, it is necessary to adjust the spray particle diameter and the amount of spray so as to fit a medicine and a patient. The reason for this is as described below.

The smaller the particle diameter of particles of a sprayed medicine is, the easier it is for particles to reach the throat, the bronchus, and further, the lungs. Accordingly, in order to improve the treatment effect, the spray particle diameter needs to be adjusted such that the medicine can be caused to efficiently reach the affected part. For example, the spray particle diameter in the case where the part to which the medicine is applied is the lungs, the spray particle diameter is set smaller than in the case where the application site is the throat.

In addition, the amount of spray needs to be adjusted in accordance with a patient breathing ability (the details of which will be described later). In the case where the amount of spray is large relative to the patient breathing ability, the patient cannot inhale all of the sprayed medicine, the medicine is wasted, and moreover, the patient will choke during the treatment, for example. In the case where the amount of spray is small relative to the patient breathing ability, a problem arises in that the treatment takes time.

Furthermore, the spray particle diameter and the amount of spray of a medicine are affected by the surface tension and the viscosity of the medicine, in addition to the hole diameter, the number of holes, and the hole shape of the mesh. For example, the amount of spray of a medicine having a large surface tension or a medicine having a high viscosity tends to be small compared with other medicines. Accordingly, when determining the hole diameter, the number of holes, and the hole shape of the mesh with which the desired output spray diameter and amount of spray can be achieved, the surface tension and the viscosity of the medicine need to be considered.

For this reason, with the above-described configuration, a patient can receive nebulizer treatment that is optimal for a medicine and the patient with minimum adjustment of the main body of a nebulizer, as a result of using a mesh selected by the nebulizer mesh selection method according to the present invention.

Here, the "medicine attribute" is obtained by classifying medicines to be used in the nebulizer into a predetermined number of attributes in advance from the viewpoint of mesh selection, and each medicine attribute is assigned an attribute number, Medicines to be applied to the same part and having surface tensions and viscosities that are close to each other are classified into the same attribute.

Note that, in the case where the number of types of medicines to be handled is small, for example, the medicine attributes and the medicine names may be in one-to-one correspondence.

The "patient breathing ability" corresponds to the amount of a medicine that the patient can inhale by breathing once, and refers to a rank of the breathing ability classified into a predetermined number of stages from the viewpoint of mesh selection.

Advantageous Effects of Invention

As described above, with the nebulizer mesh selection method according to the present invention, an optimal mesh that fits a medicine and a patient can be selected.

BRIEF DESCRIPTION OF DRAWINGS

FIG. 5 is a diagram illustrating a nebulizer mesh selection table according to an embodiment of the present invention.

FIGS. 6A and 6B are diagrams illustrating hole shapes of a nebulizer mesh according to an embodiment of the present invention.

DESCRIPTION OF EMBODIMENTS

Figure 1:
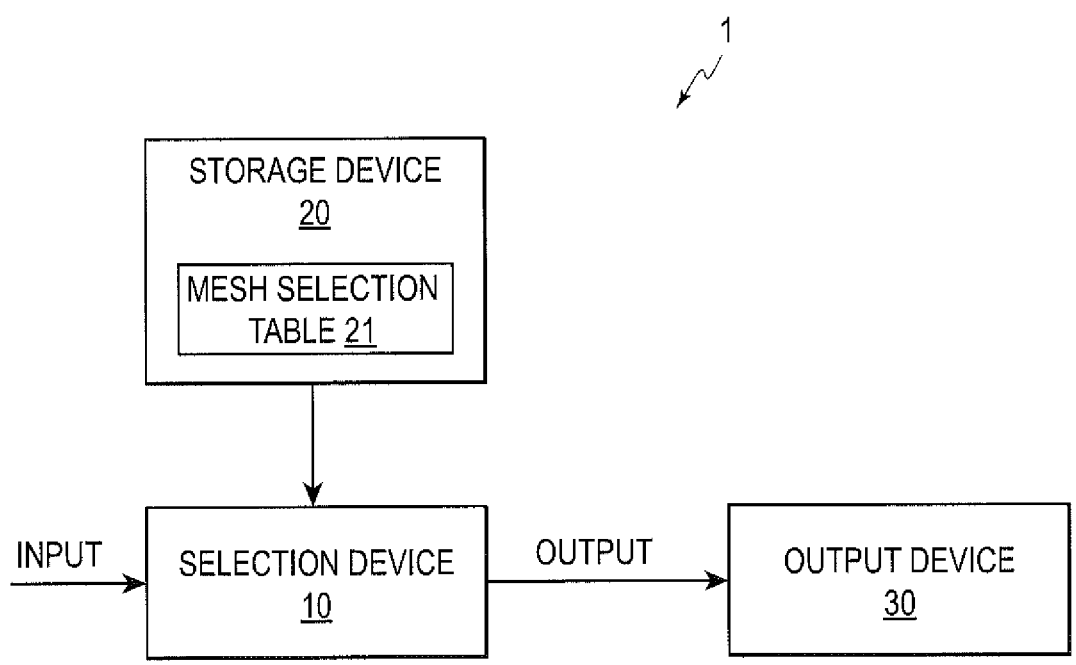
FIG. 1 is an overall configuration diagram of a nebulizer mesh selection system according to an embodiment of the present invention.

Hereinafter, an embodiment of the present invention will be described in detail with reference to the drawings. However, this embodiment is only an example, and does not give a limited construction of the present invention. Note that, in the drawings, identical or corresponding parts will be assigned an identical reference sign.

Embodiment 1

FIG. 1 is a diagram showing an overall configuration of an embodiment of a nebulizer mesh selection system 1, which is presupposed by the present invention. The nebulizer mesh selection system 1 is constituted by a storage device 20 that stores a mesh selection table 21 in which a predetermined mesh corresponds to a combination of a medicine attribute and a patient breathing ability, a selection device 10 that selects a corresponding mesh using an acquired medicine attribute and patient breathing ability based on the mesh selection table 21, and an output device 30 that outputs the corresponding mesh.

The nebulizer mesh selection system 1 according to this embodiment is used as follows, for example. A patient who suffers from asthma or the like receives a diagnosis from a doctor, and receives a prescription issued by the doctor. A medicine for a nebulizer is dispensed at a pharmacy in accordance with this prescription. At this time, upon a medicine attribute and a patient breathing ability being input to a terminal owned by the pharmacy, i.e., the selection device 10 according to this embodiment, the selection device 10 selects a nebulizer mesh that is optimal for the medicine and the patient based on the mesh selection table 21 stored in the storage device 20.

10 to 15 types of nebulizer meshes according to this embodiment that have different hole diameters, numbers of holes, and hole shapes are prepared in advance, considering versatility and productivity. An identification number is assigned to each mesh, and the output device 30 outputs the identification number of the selected mesh. A pharmacist or the like provides a patient with a mesh suitable for the medicine and the patient based on the output identification number of the mesh.

The patient sets the prescribed medicine and the mesh in the nebulizer and performs treatment. Since the spray particle diameter and the amount of spray are adjusted by the mesh so as to be optimal for the medicine and the patient, the patient can receive optimal treatment with minimum adjustment of the main body of the nebulizer.

Regarding Each Constituent Element

In this embodiment, a general-purpose personal computer is used as the selection device 10. A tablet computer, a smartphone, a mobile phone, or the like may also be used thereas.

Medicines used in the nebulizer are classified in advance into a predetermined number of attributes from the viewpoint of mesh selection. Medicines that are applied to the same part and have similar surface tensions and viscosities belong to the same attribute. The medicine attributes are identification symbols of attributes to which prescribed medicines belong. In this embodiment, the medicine attributes are managed using nine classifications that are classes 1 to 9.

The amount of spray of the nebulizer is adjusted based on the patient breathing ability. In this embodiment, breathing abilities of patients are divided into nine stages that are stages 1 to 9, in which 1 is set to be weakest and 9 is set to be strongest.

As the output device 30, a general-purpose display or the like can be used. The output thereof is not limited to visual output, and may be voice output.

Description of Flowcharts

Figure 2:
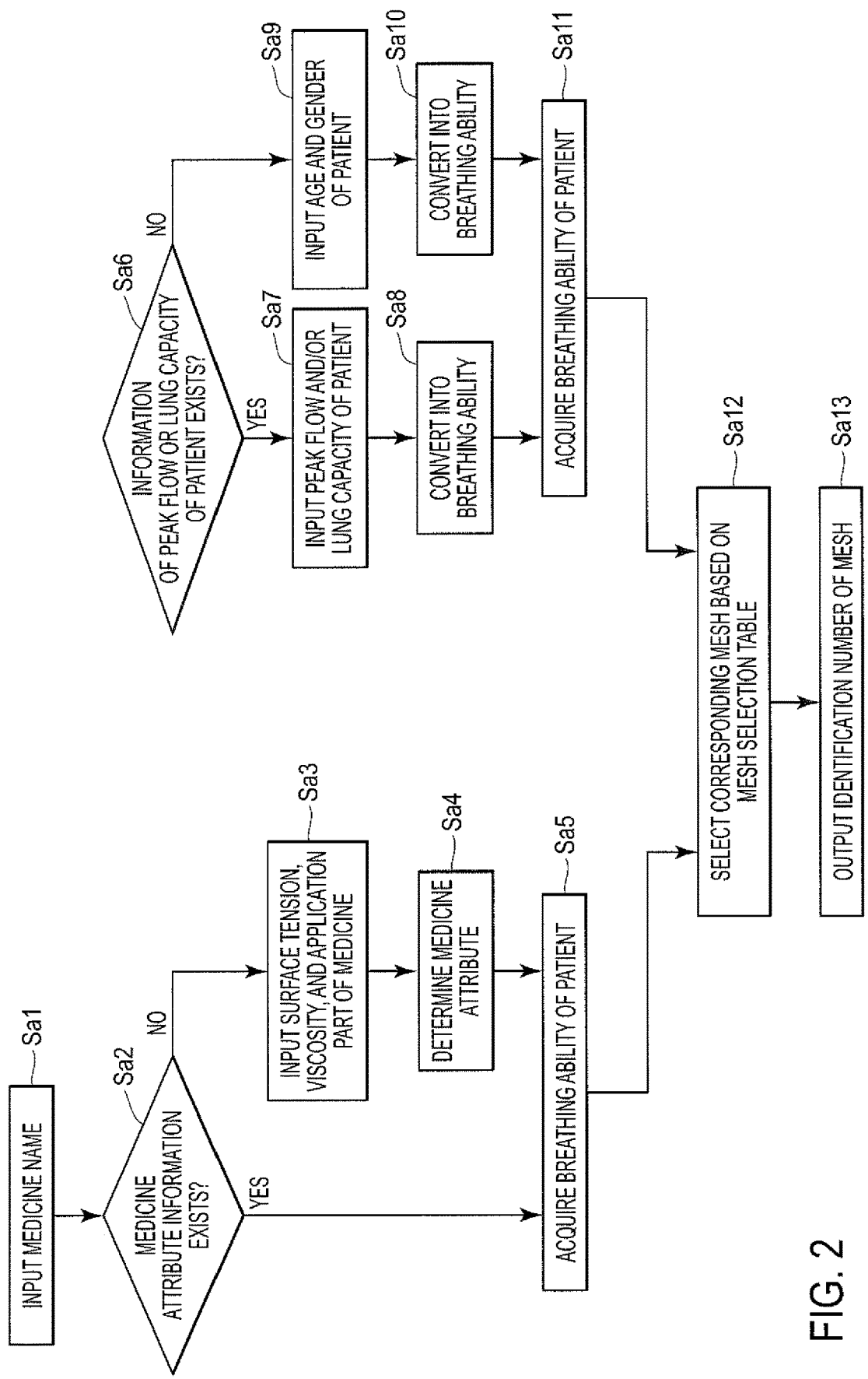
FIG. 2 is a flowchart illustrating nebulizer mesh selection processing according to an embodiment of the present invention.

FIG. 2 is a flowchart illustrating nebulizer mesh selection processing according to this embodiment. Upon a medicine to be dispensed to a patient being determined, an operator (pharmacist etc.) selects a medicine name from a pull-down menu in an input screen (step Sa1).

Note that the input of the medicine name is not limited to selection using a pull-down menu, and various methods can be used, such as input of characters using a keyboard, input using a dedicated input device, or voice input. Also, a medicine attribute may be input instead of the medicine name.

In the case where the name of the medicine to be prescribed does not exist in the pull-down menu, i.e., in the case where the attribute information about the medicine to be prescribed is not registered in the system 1 according to this embodiment (No in step Sa2), the operator selects the surface tension, the viscosity, and the application site of the medicine from pull-down menus and inputs them to the selection device 10 (step Sa3).

Note that the information regarding the medicine attributes is stored in a storage device. In this case, this storage device may be different from the storage device 20 in which the mesh selection table 21 is stored, or may be stored in the selection device 10.

This storage device has information of a reference value of the surface tension, a reference value of the viscosity, and the application site that are related to each attribute, in addition to the medicine attribute information. Accordingly, in the case where the surface tension, the viscosity, and the application site of the medicine to be prescribed are input, the medicine attribute to which this medicine belongs is determined in accordance with this information (step Sa4).

Figure 3:
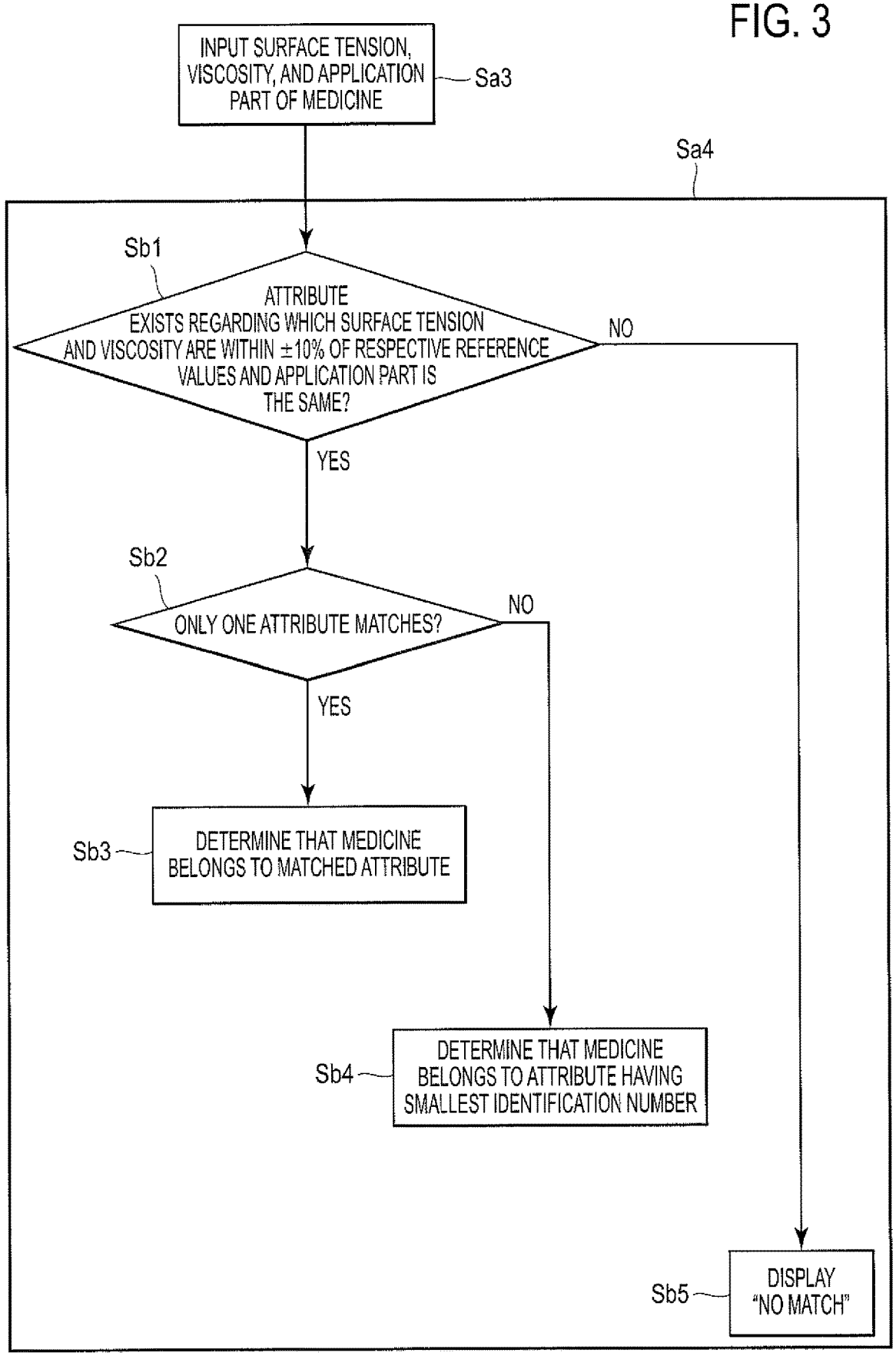
FIG. 3 is a flowchart illustrating processing for determining an attribute of a medicine according to an embodiment of the present invention.

Note that, as for step Sa4 of determining the medicine attribute, specifically, processing shown in FIG. 3 is conceivable.

Initially, medicine attributes for which the surface tension and the viscosity of the medicine that are input in step Sa3 are within ±10% from the respective reference values and the application site is the same are extracted (step Sb1).

If only one attribute matches (Yes in step Sb1, and Yes in step Sb2), the medicine is processed as belonging to this matched attribute (step Sb3).

If two or more attributes match (Yes in step Sb1, and No in step Sb2), the medicine is processed as belonging to the medicine attribute having the smallest identification number (step Sb4).

If an attribute for which the input surface tension and viscosity of the medicine are within ±10% from the respective reference values does not exist, or if an attribute with the same application site does not exist even though the surface tension and the viscosity are within ±10% from the respective reference values (No in step Sb1), a mesh for this medicine cannot be selected using the system 1, and accordingly, processing is performed such that "no match" display is output on the output device 30 (step Sb5).

Thus, even in the case of a medicine whose attribute information is not registered in advance, such as a new medicine, the medicine attribute can be determined based on the surface tension, the viscosity, and the application site thereof. Note that the aforementioned determination criteria can be changed as appropriate without departing from the gist thereof.

An operator also inputs the patient breathing ability to the selection device 10. The breathing ability can be roughly estimated from a patient age and gender, but can be more accurately determined using the patient peak flow and/or vital capacity.

For this reason, if information of the patient peak flow and/or vital capacity exists (Yes in step Sa6), the operator inputs the patient peak flow and/or vital capacity to the selection device 10 (step Sa7). This input information is converted into the breathing ability based on a predetermined conversion table (step Sa8).

If the information of the patient peak flow and/or vital capacity does not exist (No in step Sa6), the operator inputs the patient age and gender in place of the patient peak flow and/or vital capacity (step Sa9). This input information is converted into the patient breathing ability based on a predetermined conversion table (step Sa10).

Note that the "peak flow" refers to the speed of a breath when fully breathing out from a state of having deeply breathed in.

In general, the patient age and gender are described in the prescription. Accordingly, even if the information of the patient peak flow and/or vital capacity does not exist, the patient breathing ability can be estimated using the patient age and gender without performing special examination or measurement, and a mesh that is optimal for the medicine and the patient can be selected.

The patient breathing ability acquired through steps Sa8 or Sa10 described above is input to the storage device 20 (step Sa11).

Using the nebulizer mesh selection table 21 stored in the storage device 20, the selection device 10 selects a mesh that is optimal for the medicine and the patient based on the medicine attribute acquired in step Sa5 and the patient breathing ability acquired in step Sa11 (step Sa12). The identification number of the selected mesh is transmitted from the selection device 10 to the output device 30, and the output device 30 outputs this identification number of the mesh (step Sa13).

Note that in the case where the mesh selection system 1 according to this embodiment handles a small number of types of medicine, for example, the medicine attributes may be in one-to-one correspondence with medicine names. In this case, the selection device 10 may be configured to select an optimal mesh based on a mesh selection table in which a predetermined mesh corresponds to a combination of the medicine name and the patient breathing ability, without converting the medicine name into the medicine attribute.

Regarding Mesh Selection Flow

Figure 4:
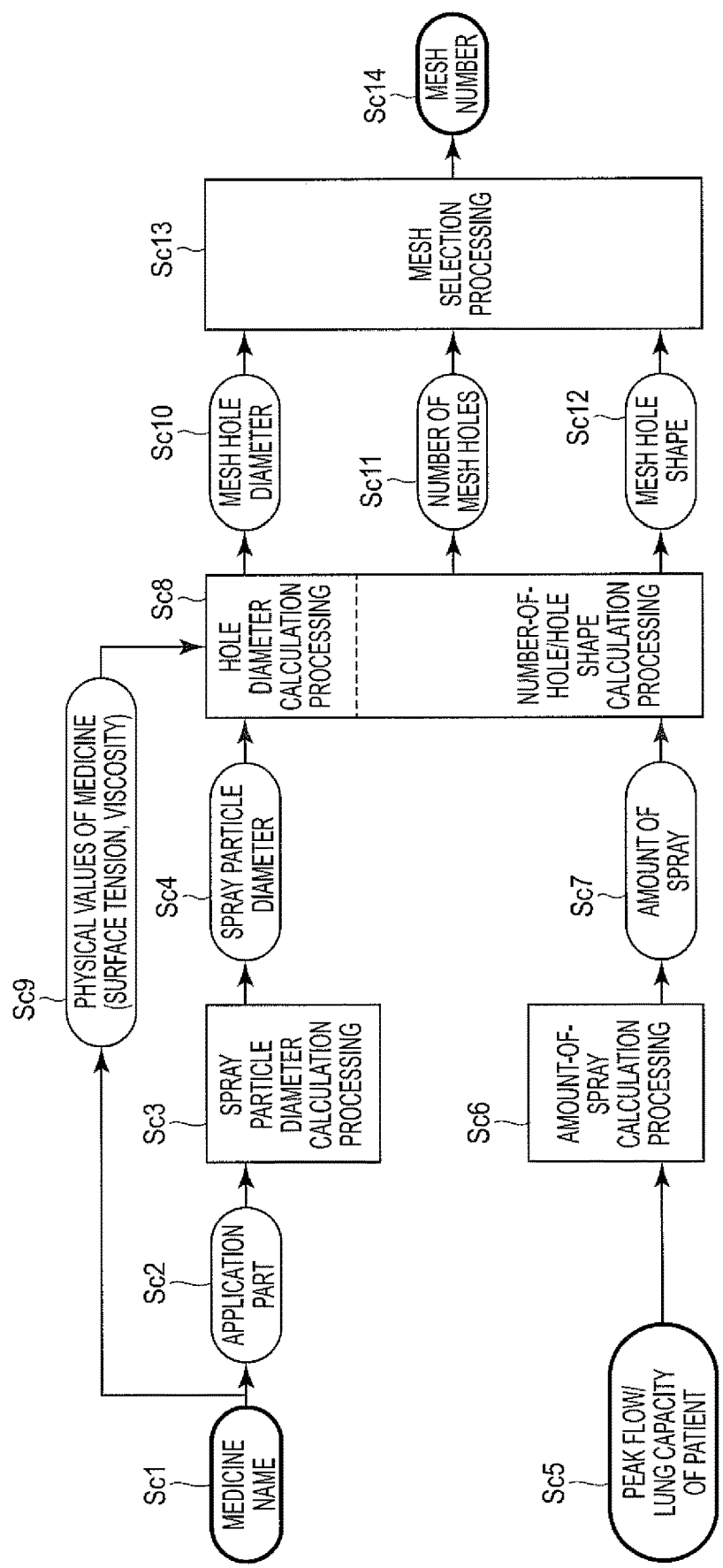
FIG. 4 is a diagram illustrating a specific processing flow of mesh selection according to an embodiment of the present invention.

FIG. 4 is a diagram illustrating a specific processing flow of mesh selection according to this embodiment. For the sake of simplicity, a description will be given of a mesh selection method in the case where a medicine name as well as a patient peak flow and vital capacity have been input.

Initially, the operator inputs the medicine name (step Sc1). The system 1 has information of the surface tension, viscosity, and application site of the medicine that corresponds to the medicine name. The selection device 10 acquires the application site that corresponds to the medicine name (step Sc2). The spray particle diameter is determined in accordance with the application site of the medicine (steps Sc3 and Sc4). The farther the affected part, such as the throat, the bronchus, or the lungs, is from the mouth cavity, the smaller the spray particle diameter is set Note that, in the case where a plurality of application sites that correspond to the medicine name are conceivable, the application site cannot be specified. In this case, information of the application site may be acquired by receiving input from the operator that is based on the information on the prescription.

The operator also inputs the patient peak flow and vital capacity (step Sc5). The patient breathing ability is determined based on the above information, and the amount of spray that fits the patient breathing ability is determined (steps Sc6 and Sc7).

The hole diameter, the number of holes, and the hole shape of the mesh that achieve the spray particle diameter determined in step Sc4 and the amount of spray determined in step Sc7 are obtained by calculation (step Sc8).

Note that the ease of dispensing the medicine is affected by the physical properties of the medicine such as the surface tension and the viscosity, the physical values of the medicine are considered when calculating the hole diameter, the number of holes, and the hole shape of the mesh (steps Sc8 and Sc9).

The hole diameter, the number of holes, and the hole shape of the mesh are determined by the calculation processing in step Sc8 (steps Sc10, Sc11, and SC12).

10 to 15 types of meshes having different hole diameters, number of holes, and hole shapes are prepared in advance, considering versatility and productivity. A mesh whose hole diameter, number of holes, and hole shape are closest to the hole diameter, the number of holes, and the hole shape that are determined by the calculation processing in step Sc8 is selected from among those meshes (step Sc13). The identification number of the selected mesh is displayed on the output device 30 (step Sc14).

Thus, in the processing flow of mesh selection shown in FIG. 4, the mesh is selected in step Sc14 through various kinds of processing using the medicine name that is input in step Sc1 and the patient peak flow and vital capacity that are input in step Sc5. Therefore, in the embodiment shown in FIGS. 1 and 2, the medicine attribute, the patient breathing ability, and a mesh number selected based on this information are stored in advance in a table. With this configuration, the processing can be simplified, and a processing load on the selection device 10 can be reduced. Note that a configuration may be employed in which, instead of using the mesh selection table, the selection device 10 is caused to perform the processing shown in FIG. 4 in real-time.

FIG. 5 shows an example of the nebulizer mesh selection table 21 stored in the storage device 20. Meshes that correspond to the medicine attributes and the patient breathing abilities are defined therein.

FIGS. 6A and 6B are diagrams showing the shapes of holes of the nebulizer meshes according to this embodiment.

A through-hole 43 in FIG. 6A has a circular-cone cross-sectional shape. Medicine is supplied from an inlet surface 41 of a mesh 40, passes through the through-hole 43, and is atomized from an outlet surface 42 of the mesh 40. The through-hole 43 has a tapered shape so as to be narrower from the inlet surface 41 of the mesh 40 toward the outlet surface 42 of the mesh 40, and the taper angle is θ.

A through-hole 43 in FIG. 6B has a horn-like cross-sectional shape. The taper angle is θ as in FIG. 6A, but the cross-sectional shape of the through-hole 43 is further widened on the side of the inlet surface 41 of the mesh 40 than in FIG. 6A. For this reason, the medicine can more easily enter the through-hole 43 than in FIG. 6A, and the amount of spray is larger.

As described above, with the nebulizer mesh selection system 1 according to this embodiment, an optimal mesh that fits a medicine and a patient can be selected. The patient can receive optimal treatment by setting this mesh in the nebulizer, with minimum adjustment of the main body of the nebulizer.

REFERENCE SIGNS LIST

1 Mesh selection system
10 Selection device
20 Storage device
21 Mesh selection table
30 Output device
40 Mesh
41 Inlet surface
42 Outlet surface
43 Through-hole

The invention claimed is:

1. A mesh selection system for a replaceable-mesh nebulizer, which is configured to accept one of a plurality of meshes of different types having different hole sizes and different hole numbers, the mesh selection system comprising:
a terminal;
a memory that stores a mesh selection table in which the meshes of different types are classified; and
a computer configured to:
prepare the mesh selection table in which the meshes of different types are classified, the mesh selection table defining a plurality of medicine attributes and a plurality of patient breathing abilities,
wherein: (i) the meshes of different hole sizes are classified based on the determined spray particle diameter in consideration of the acquired application site and the acquired identification symbol, and (ii) the meshes of different hole numbers are classified based on the determined amount of spray in consideration of the acquired category;
acquire an application site representing a place in the body of a patient where medicine should be applied;
determine the spray particle diameter based on the acquired application site;
acquire a category associated with a breathing ability of the patient;
determine an amount of spray based on the acquired category;
acquire an identification symbol associated with a medicine attribute, the medicine attribute including a surface tension and a viscosity of the medicine;
calculate a hole diameter, a number of holes, and a hole shape of the mesh based on the acquired medicine attribute, the amount of spray, and patient breathing ability;
select, from the mesh selection table, a mesh having a hole diameter, number of holes, and hole shape that are closest to the calculated hole diameter, number of holes, and hole shape; and
display an identifier of the selected mesh to the terminal,
wherein the selected mesh is provided to the patient and is suitable for the medicine and a condition of the patient based on the displayed identifier of the selected mesh.

2. The mesh selection system for a replaceable-mesh nebulizer according to claim 1,
wherein the computer acquires a medicine name and converts the acquired medicine name into a medicine attribute based on a table in which the medicine name is associated with the medicine attribute.

3. The mesh selection system for a replaceable-mesh nebulizer according to claim 2,
wherein the medicine name and the medicine attribute are in one-to-one correspondence.

4. The mesh selection system for a replaceable-mesh nebulizer according to claim 1,
wherein the computer acquires the surface tension, the viscosity and the application site of the medicine, and determines the medicine attribute based on the acquired surface tension, viscosity, and application site of the medicine.

5. The mesh selection system for a replaceable-mesh nebulizer according to claim 4,
wherein the computer determines a medicine attribute such that the acquired application site of the medicine is the same as an application site of a medicine related to the medicine attribute to be determined, and the acquired surface tension and viscosity of the medicine are respectively within predetermined ranges from a surface tension reference value and a viscosity reference value of the medicine related to the medicine attribute to be determined.

6. The mesh selection system for a replaceable-mesh nebulizer according to claim 5,
wherein the predetermined ranges are each ±10%.

7. The mesh selection system for a replaceable-mesh nebulizer according to claim 1,
wherein the computer acquires a patient age, and converts the acquired patient age into a patient breathing ability based on a table in which a patient age is associated with a patient breathing ability.

8. The mesh selection system for a replaceable-mesh nebulizer according to claim 1, wherein the computer acquires a patient age and a patient gender, and converts the acquired patient age and patient gender into a patient breathing ability based on a table in which a patient age and a patient gender are associated with a patient breathing ability.

9. The mesh selection system for a replaceable-mesh nebulizer according to claim 1,
wherein the computer acquires a patient peak flow and/or vital capacity, and converts the acquired patient peak flow and/or vital capacity into a patient breathing ability based on a table in which a patient peak flow and/or vital capacity are associated with a patient breathing capacity.

10. A computer-readable non-transitory medium storing a mesh selection table and a program for causing a computer to execute a nebulizer mesh selection method of selecting a mesh from a plurality of meshes of different types having different hole sizes and different hole numbers, the method comprising:
preparing the mesh selection table in which the meshes of different types are classified, the mesh selection table defining a plurality of medicine attributes and a plurality of patient breathing abilities,
wherein: (i) the meshes of different hole sizes are classified based on the determined spray particle diameter in consideration of the acquired application site and the acquired identification symbol, and (ii) the meshes of different hole numbers are classified based on the determined amount of spray in consideration of the acquired category;

acquiring an application site representing a place in the of a body patient where the medicine should be applied;
determining the spray particle diameter based on the acquired application site;
acquiring a category associated with a breathing ability of the patient;
determining an amount of spray based on the acquired category;
acquiring, by the computer, an identification symbol associated with a medicine attribute, the medicine attribute including a surface tension and a viscosity of the medicine;
calculating a hole diameter, a number of holes, and a hole shape of the mesh based on the acquired medicine attribute, the amount of spray, and patient breathing ability;
selecting, from the mesh selection table, a mesh having a hole diameter, number of holes, and hole shape that are closest to the calculated hole diameter, number of holes, and hole shape; and
displaying an identifier of the selected mesh to the terminal,
wherein the selected mesh is provided to the patient and is suitable for the medicine and a condition of the patient based on the displayed identifier of the selected mesh.

* * * * *